(12) United States Patent
Liu et al.

(10) Patent No.: US 12,376,815 B2
(45) Date of Patent: *Aug. 5, 2025

(54) ARTIFICIAL INTELLIGENCE BASED DIAGNOSIS WITH MULTIPLE PULSED X-RAY SOURCE-IN-MOTION TOMOSYNTHESIS IMAGING SYSTEM

(71) Applicants: Jianqiang Liu, Campbell, CA (US); Manat Maolinbay, Gilroy, CA (US); Chwen-Yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-Yuan Ku, San Jose, CA (US); Linbo Yang, Pleasanton, CA (US)

(73) Assignee: AIX Inc., Sunnyvale, CA (US)

( * ) Notice: Subject to any disclaimer, the term of this patent is extended or adjusted under 35 U.S.C. 154(b) by 670 days.

This patent is subject to a terminal disclaimer.

(21) Appl. No.: 17/564,059

(22) Filed: Dec. 28, 2021

(65) Prior Publication Data
US 2022/0319007 A1 Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2024.01)
*A61B 6/02* (2006.01)
(Continued)

(52) U.S. Cl.
CPC .............. *A61B 6/541* (2013.01); *A61B 6/025* (2013.01); *A61B 6/032* (2013.01); *A61B 6/035* (2013.01);
(Continued)

(58) Field of Classification Search
CPC ......... A61B 6/541; A61B 6/025; A61B 6/032; A61B 6/5211; G06T 7/0012;
(Continued)

(56) References Cited

U.S. PATENT DOCUMENTS

4,716,581 A * 12/1987 Barud .................. A61B 6/4441
378/197
5,550,889 A * 8/1996 Gard ..................... H01J 35/153
378/121
(Continued)

*Primary Examiner* — Vincent Rudolph
*Assistant Examiner* — Timothy Choi
(74) *Attorney, Agent, or Firm* — PatentPC; Bao Tran (57) ABSTRACT

The presented are X-ray diagnosis method and system using multiple pulsed X-ray source-in-motion tomosynthesis imaging technology. While taking X-ray instrument image data, artificial intelligence (AI) analyzes patient responses, compares current condition with the patient history and other patient information that may become part of a patient. It reports lesions location changes, sets severity threshold and warning status, generate treatment information. It also recommend to a X-ray region of interest (ROI) scan, a complete X-ray CT scan or other health care professionals and specialists.

20 Claims, 3 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| A61B 6/03 | (2006.01) | |
| A61B 6/04 | (2006.01) | |
| A61B 6/06 | (2006.01) | |
| A61B 6/08 | (2006.01) | |
| A61B 6/40 | (2024.01) | |
| A61B 6/42 | (2024.01) | |
| A61B 6/46 | (2024.01) | |
| A61B 6/58 | (2024.01) | |
| G01N 23/044 | (2018.01) | |
| G01N 23/083 | (2018.01) | |
| G01N 23/18 | (2018.01) | |
| G06T 7/00 | (2017.01) | |
| G06T 7/11 | (2017.01) | |
| G06T 11/00 | (2006.01) | |
| G06T 17/00 | (2006.01) | |
| G06V 10/25 | (2022.01) | |
| G06V 10/62 | (2022.01) | |
| G16H 10/60 | (2018.01) | |
| G16H 30/20 | (2018.01) | |
| G16H 50/20 | (2018.01) | |
| A61B 6/50 | (2024.01) | |

(52) U.S. Cl.
CPC .............. *A61B 6/0407* (2013.01); *A61B 6/06* (2013.01); *A61B 6/08* (2013.01); *A61B 6/4007* (2013.01); *A61B 6/4014* (2013.01); *A61B 6/4021* (2013.01); *A61B 6/405* (2013.01); *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(58) Field of Classification Search
CPC ....... G06T 7/0016; G06T 7/11; G06T 11/003; G06T 2207/10076; G06T 2207/10081; G06T 2207/20081; G06T 2207/20084; G06T 2207/30096; G06T 2211/412; G06V 10/25; G06V 10/62; G06V 2201/032; G06V 2201/03; G16H 10/60; G16H 30/20; G16H 50/20
See application file for complete search history.

(56) References Cited

U.S. PATENT DOCUMENTS

| | | | | |
|---|---|---|---|---|
| 5,919,267 | A * | 7/1999 | Urnes | G06F 11/0751 714/E11.026 |
| 7,194,061 | B2 * | 3/2007 | Fujita | A61B 6/4028 378/150 |
| 8,559,591 | B2 * | 10/2013 | Boese | A61B 6/4014 378/9 |
| 11,617,556 | B2 * | 4/2023 | Liu | G06T 7/0012 378/9 |
| 11,617,557 | B2 * | 4/2023 | Liu | A61B 6/025 378/197 |
| 11,633,168 | B2 * | 4/2023 | Liu | A61B 6/482 378/9 |
| 11,730,439 | B2 * | 8/2023 | Liu | A61B 6/56 378/197 |
| 11,766,231 | B2 * | 9/2023 | Liu | A61B 6/4233 378/22 |
| 11,857,359 | B2 * | 1/2024 | Liu | G06V 10/62 |
| 11,918,403 | B2 * | 3/2024 | Liu | A61B 6/025 |
| 12,023,193 | B2 * | 7/2024 | Liu | G06T 7/0016 |
| 12,102,469 | B2 * | 10/2024 | Liu | G06T 11/005 |
| 2004/0109529 | A1 * | 6/2004 | Eberhard | A61B 6/4028 378/23 |
| 2007/0025509 | A1 * | 2/2007 | Pang | A61B 6/025 378/65 |
| 2007/0248213 | A1 * | 10/2007 | Dolgonos | H05G 1/20 378/106 |
| 2012/0189094 | A1 * | 7/2012 | Neushul | A61B 6/035 378/19 |
| 2012/0195403 | A1 * | 8/2012 | Vedantham | A61B 6/022 378/62 |
| 2012/0300901 | A1 * | 11/2012 | Lewalter | H01J 35/13 378/126 |
| 2014/0086380 | A1 * | 3/2014 | Song | H01L 23/373 378/4 |
| 2016/0056008 | A1 * | 2/2016 | Mackie | H01J 35/13 378/5 |
| 2019/0131016 | A1 * | 5/2019 | Cohen | A61B 6/032 |
| 2019/0388050 | A1 * | 12/2019 | Lee | A61B 6/54 |
| 2020/0085382 | A1 * | 3/2020 | Taerum | G06T 7/0016 |
| 2020/0202620 | A1 * | 6/2020 | Kiely | A61B 6/032 |
| 2020/0345318 | A1 * | 11/2020 | Turner | A61B 6/4464 |
| 2021/0093275 | A1 * | 4/2021 | Hoernig | A61B 6/4035 |
| 2021/0177371 | A1 * | 6/2021 | Wang | A61B 90/39 |
| 2022/0028524 | A1 * | 1/2022 | Levi | G16H 30/20 |
| 2022/0179026 | A1 * | 6/2022 | Zaiss | G06T 7/11 |
| 2022/0245482 | A1 * | 8/2022 | Inamdar | G16H 40/63 |

* cited by examiner

ARTIFICIAL INTELLIGENCE BASED DIAGNOSIS WITH MULTIPLE PULSED X-RAY SOURCE-IN-MOTION TOMOSYNTHESIS IMAGING SYSTEM

The present invention claims priority to Provisional Application Ser. No. 63/182,426 filed on Apr. 30, 2021; 63/226,508 filed Jul. 28, 2021; 63/170,288 filed Apr. 2 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

The current invention generally relates to artificial intelligence (AI) based method and system for diagnosis of lung and breast disease, and, more particularly, to a method system for artificial intelligence (AI) based diagnosis with multiple pulsed X-ray source-in-motion tomosynthesis imaging systems.

BACKGROUND

Tomosynthesis, also Digital Tomosynthesis (DTS), is a method for performing high-resolution limited-angle tomography at radiation dose levels comparable with projection radiography. It has been studied for a variety of clinical applications, including vascular imaging, dental imaging, orthopedic imaging, mammographic imaging and lung imaging. The big advantage is that the DTS X-ray dose level is far less than that of a CT imaging. DTS is also much faster than that of CT and costs far less.

Multiple pulsed X-ray source-in-motion tomosynthesis imaging system is a new type of DTS. It can run even faster and cover much wider angles than that of regular single source DTS. It can be used for rapid lung cancer screen, breast cancer screen. Whole screen process only last only several seconds.

Although new type of DTS is ultra-fast, currently it still relies primarily on human medical doctors for diagnosis purposes. Therefore, the overall overhead will add up to slow down the diagnosis process. In order to perform fast lung cancer screening and breast cancer screening for everybody, it is therefore desirable to provide much improved systems and methods for diagnosing lung or breast conditions. Artificial Intelligence based diagnosis is becoming necessary.

SUMMARY

The presented are X-ray diagnostic methods using multiple pulsed source in-motion tomosynthesis imaging systems. While taking X-ray instrument image data, artificial intelligence (AI) analyzes responses from patient, compares current condition with the patient history and other patient information in local computer or in neural network that may become part of a patient. It reports lesion location changes, sets severity threshold and warning status, generates treatment information. It also recommends a region of interest (ROI) scan, a complete CT scan, or other health care professionals and specialists.

Advantages of the system may include one or more of the following. The system leverages the high speed of DTS with computer learning for diagnostics purposes. AI is used as a diagnostics tool is used to speed up the data acquisition and diagnosis decisions.

Multiple pulsed X-ray source-in-motion tomosynthesis imaging system is a rapid X-ray diagnosis apparatus. It can perform a nearly real-time low-dose X-ray scan. It is also possible to perform 4D scans and progressive scans. AI can also manage all the processes associated with the superfast tomosynthesis imaging system with very little human intervention.

Before performing a scan, a normal AI model is created from the collection of the selected data, and an anomaly measure is found, whereas a threshold value is determined. Subsequently, an anomaly measure is found from the newly acquired data, and the created a normal model. Then, this anomaly measure is compared with the new threshold value in order to detect an anomaly of the apparatus.

Nowadays, computers and networks are fast and local storage is also large, fast and low cost. For a standalone system, while the network is not conveniently accessible, the lesion diagnosis system can preferably be implemented in software running locally.

The lesion diagnosis system is also implemented in software running in a neural network for a networked system. The lesion diagnosis system constructs a model of the performance of each subsystem in a normal operating mode and each of a plurality of different possible failure modes.

Then, the AI preferably dynamically predicts the performance of each subsystem based upon the response of each of the models to dynamically changing operating conditions, compares the actual performance and result of each subsystem with the dynamically predicted performance thereof in each of the normal and possible failure modes, and determines the operating condition based on these comparisons.

Using AI, it is possible to take the progressive scan at the data acquisition stage. After getting the result from a partial scan, AI can immediately decide if a continuing scan is desirable. It will stop if enough information is collected.

AI behaves like a doctor, and AI scan behaves like a doctor's visit for a patient. If there is no changes, it probably means everything is ok. Then the process will stop. If there are some changes found, AI will decide to find out how much is changes and where the location is. Then AI also makes a decision on how serious it is. If it is not serious, then the process is finished. If it is serous, AI will generate a warning to doctors and send recommendations to do a region of interest (ROI) scan or CT scan or even other more comprehensive diagnostic tools.

DETAILED DESCRIPTION

In the following paragraphs, the present invention will be described in detail by way of example with reference to the attached drawings. Throughout this description, the preferred embodiment and examples shown should be considered exemplars rather than limitations on the present invention. As used herein, the "present invention" refers to any one of the embodiments of the invention described herein and any equivalents. Furthermore, reference to various feature(s) of the "present invention" throughout this document does not mean that all claimed embodiments or methods must include the referenced feature(s).

This invention may, however, be embodied in many different forms and should not be construed as limited to the embodiments set forth herein. These embodiments are provided so that this disclosure will be thorough and complete and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

The present invention is related to medical diagnostic methods using multiple pulsed source in-motion tomosynthesis imaging system. The primary object of the present invention is to provide a method for image-based lesion diagnostics. The second object of the present invention is to provide image-based lesion diagnostics with artificial intelligence (AI) assistance. While taking X-ray instrument image data, AI analyzes patient responses, compares current condition with the patient history and other patient information that may become part of a patient. It reports lesion location changes, sets severity threshold and warning status, generates treatment information. It also recommends a region of interest (ROI) scan, a complete CT scan, or other health care professionals and specialists. A superfast multiple pulsed X-ray Source In-motion tomosynthesis imaging system is designed. A dynamic change will occur due to sudden equipment breakdowns during the system run. However, it can be properly diagnosed and analyzed by comparing it with normal system response.

Figure 1:
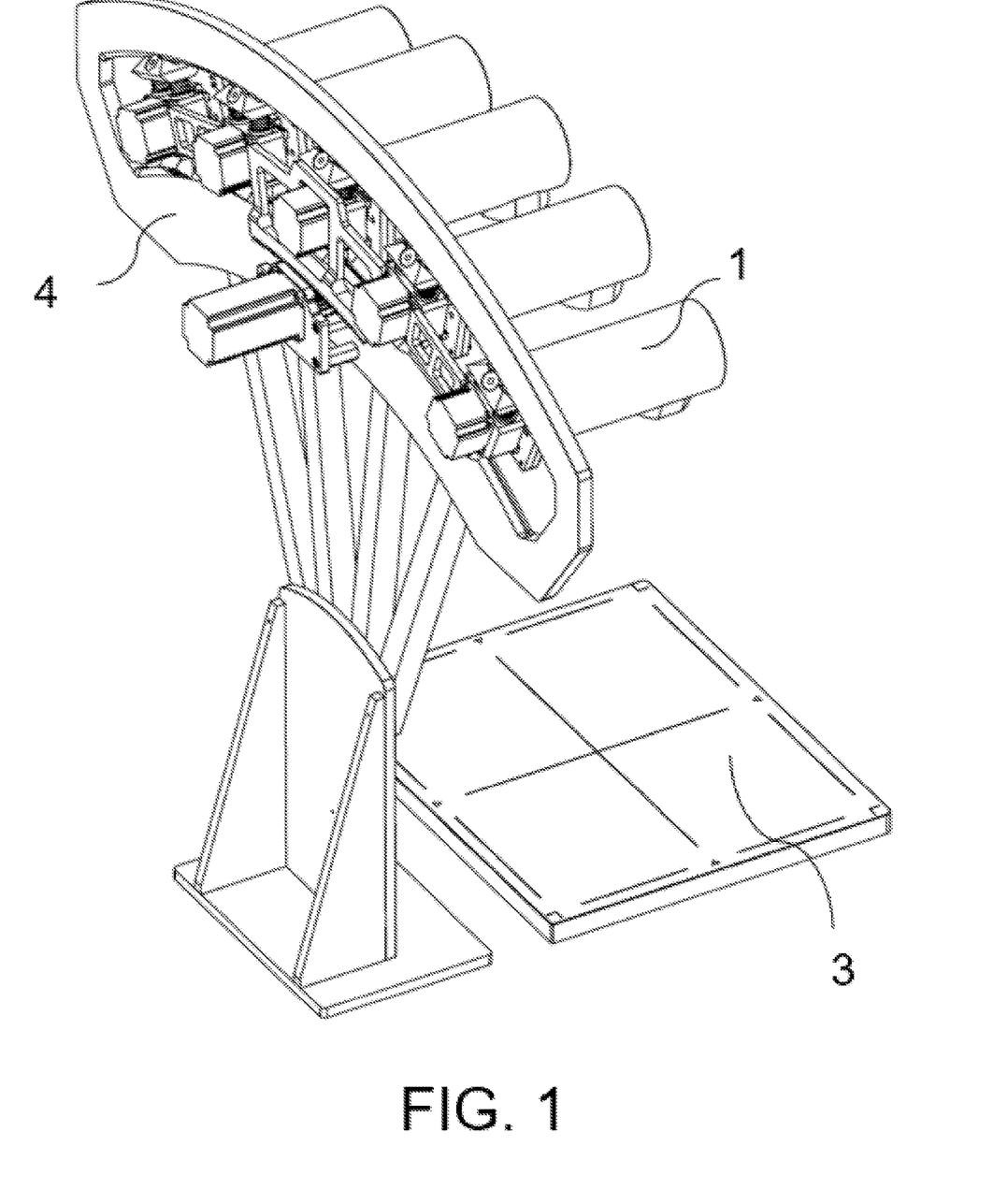
FIG. 1 illustrates an exemplary multiple pulsed X-ray source in-motion tomosynthesis imaging system.

In one embodiment, FIG. 1 shows a new type of X-ray imaging system. It is multiple pulsed X-ray source-in-motion tomosynthesis imaging system 4 to perform highly efficient and ultrafast 3D radiography. There are multiple pulsed X-ray sources mounted on a structure in motion to form an array of sources. The multiple X-ray sources move simultaneously relative to an object on a pre-defined arc track at a constant speed as a group. Each individual X-ray source can also move rapidly around its static position at a small distance. When an X-ray source has a speed equal to group speed but with opposite moving direction, the X-ray source and X-ray flat panel detector are activated through an external exposure control unit to stay standstill momentarily. It results in a much-reduced source travel distance for each X-ray source. As a result, the 3D scan can cover a much wider sweep angle in a much shorter time, and image analysis can also be done in real-time. This type of X-ray machine utilizes much more X-ray sources than other types of X-ray image machines in order to achieve a much higher scan speed.

Multiple X-ray sources are mounted on a rotating gantry. X-ray source(s) emit(s) a pulsed x-ray beam(s) toward a target that a patient may image. In-motion imaging device acquires image data from a region of interest as the patient moves from left to right. An in-motion imaging device preferably includes a microprocessor that collects and processes X-ray images of the patient, compares these images with reference images acquired earlier, and generates various outputs. Data acquisition may be performed using any one of the numerous digital image acquisition systems currently available for collecting digital image data. Examples of such devices include X-ray panel detector, either flat or curved.

X-ray flat panel detector 3 receives X-ray beam. The flat panel detector is comprised of an array of pixels. Each pixel has individual intensity value corresponding to received X-ray energy at the position of that pixel. At each moment of time, each pixel can receive X-ray radiation or no X-ray radiation depending on the number of times of exposure to the X-ray source within a time interval. The flat panel detector is placed in close proximity to the X-ray source and subject during scanning. It receives X-ray photons from an X-ray source. The intensity of each pixel value will depend on the magnitude of the X-ray photon's energy, which arrives at that pixel's position. As a result, a single pixel may have a variety of pixel values based on a variety of X-ray photons energies. These pixel values represent a response of a detector to a particular X-ray imaging modality. The specific modality depends on the application and the imaging parameters used during acquisition. X-ray detectors can be used as stand-alone devices or as part of a larger imaging system.

The supporting frame structure includes a substantially planar base, a substantially vertical supporting member, and a rotatable frame portion rotatably mounted to the supporting member. The frame structure is sized and configured to support the X-ray tube at a preselected angular orientation with respect to the patient on the movable platform. This allows the frame portion to rotate freely about the pivot arm. This configuration allows the angular orientation of the X-ray tube to be varied as needed during a scan procedure without requiring rotation of the supporting member or base. It will be appreciated that other configurations for mounting the frame portion to the base are possible without departing from the scope of the present invention.

Figure 2:
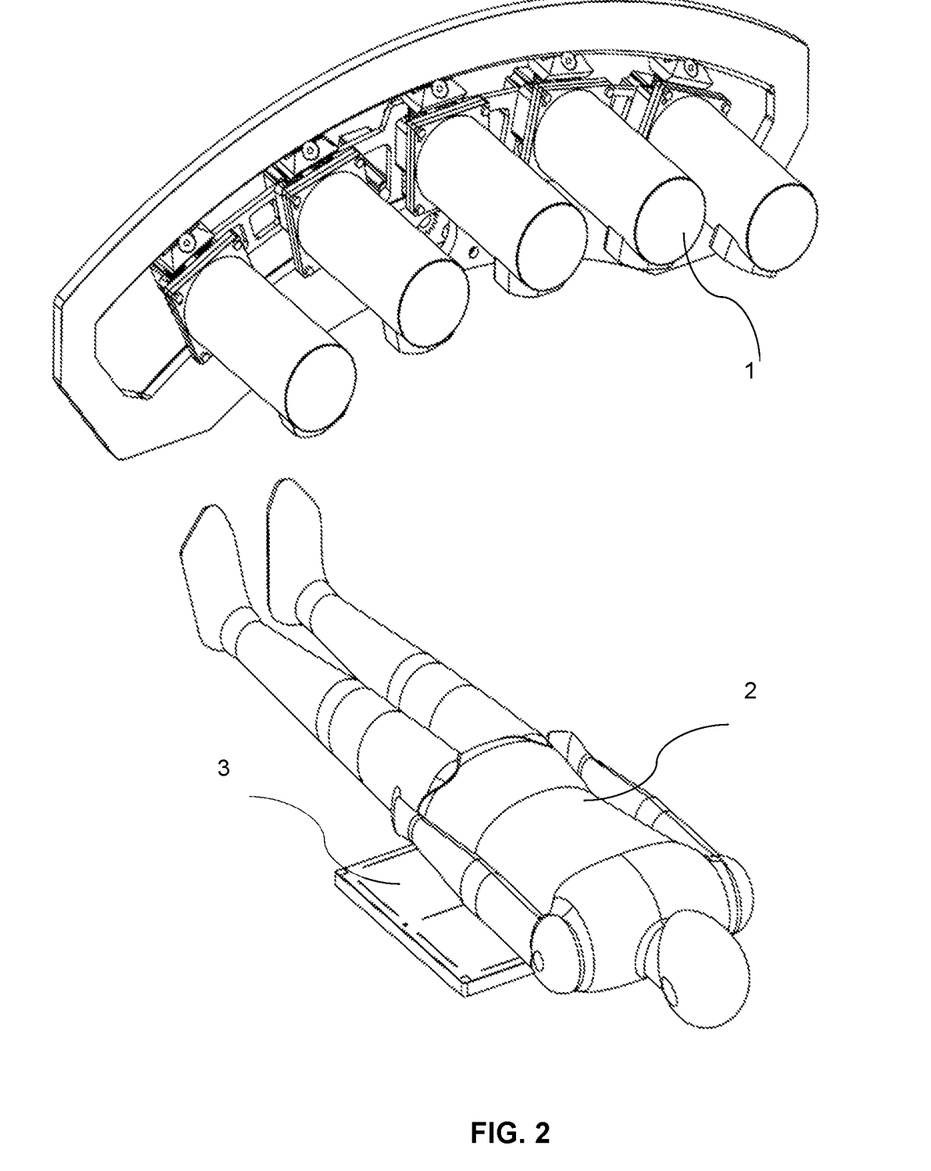
FIG. 2 shows an exemplary diagnosis scan of a patient object.

FIG. 2 shows a diagnosis scan of a patient 2 or an object. The novel X-ray imaging system uses multiple pulsed X-ray sources in motion to perform X-ray imaging primarily for lung imaging or breast mammography. It can easily take up to 120 degrees or more to scan in a few seconds. It already can cover a relatively wide span angle from the first set of a scan to start with. For example, for a five source and total 25 scan system, X-ray data set from firing sequence is the first set of 1-6-11-16-21; the second set of 2-7-12-17-22; the third set of 3-8-13-18-23; the fourth set of 4-9-14-19-24; the fifth set of 5-10-15-20-25 and so on. For five sources, this type of machine can easily go to above total 120 scans or more. After the first set of data is acquired, AI can immediately preform diagnostics without waiting for the second sets. In FIG. 2, There are multiple X-ray sources 1, a patient 2 is placed in front of an X-ray flat panel detector 3.

Multiple pulsed X-ray source-in-motion tomosynthesis imaging system 4 uses high speed pulsed X-ray sources to perform a progressive scan, near real-time low dose tomosynthesis imaging. The acquisition of multiple sequential in-motion tomosynthesis images are combined to form a higher-resolution image or video, but no two sequential images overlap. Progressive scan is typically achieved by simultaneously performing imaging at two or more separate locations, using different tomosynthesis protocols for each. Multiple x-ray sources are preferably distributed along the tomosynthesis around the examination subject to obtain high-resolution X-ray images in any desired cross-sectional planes. A dedicated radiographic plate collects the incident X-rays and directs them to corresponding flat panel detectors via suitable collimators. Progressive scan using multiples sources has shown some advantages such as speed and spatial resolution. Multiple exposures from the same set of tomosynthesis data can be merged into a higher-resolution image while not losing any diagnostic information. Therefore, one does not need to rescan the patient again with a higher-resolution scan technique to get a better quality image. This increases efficiency and reduces radiation exposure of the patient and healthcare provider.

In this vertical configuration, a patient 2 is placed on an X-ray table. In other horizontal configuration, a patient 2 can stand between X-ray sources 1 and X-ray flat panel detector 3. An operator or user of the system directs or controls the overall procedure using the user interface, which includes a display for visualizing the selected data. A workstation (not shown) with its processing power can be used instead of the user interface to control the overall procedure. The user interface is connected via network interface to the local storage main memory and processors. The superfast X-ray source 1 directs multiple pulsed X-ray beams at the patient.

X-ray flat panel detector 3, X-ray source 1, and collimator can be mounted on a table or movable mount. The construction and operating principle of each of these elements is known in the art. The beam emitted by X-ray source passes through the patient, then collimator then is reflected back into the patient by the beam splitter. A multiple pulsed X-ray source-in-motion tomosynthesis imaging system 4 is a superfast X-ray diagnosis apparatus. In order to achieve this goal, one aspect of the disclosed invention includes the design of multiple pulsed X-ray source-in-motion tomosynthesis imaging system 4 that has a high rate of data acquisition. It also provides a detailed X-ray imaging scan.

During 3D X-ray imaging, artificial intelligence (AI) allows computer systems to perform tasks that requires human intelligence, such as visual perception, image recognition and decision-making. These kinds of tasks need cognitive functions associated with human minds, namely learning and problem solving. Machine learning is a subset of AI Machine learning may be implemented utilizing deep learning (DL) process. DL is a machine learning method that employs mathematical models called neural networks. Neural networks may include large number of steps that attempt to mimic the human brain. When X-ray imaging operation is performed, DL attempts to extract complex hierarchal features and patterns present in large image datasets. These features may then be merged together using neural networks to represent the model of the X-ray image data.

Described herein are AI-based systems and methods for lung or breast diagnosis, such as assisting in the discovery of lung, breast cancer or nodule conditions after AI model is already established though large amount of X-ray imaging data from real patients. The AI-based systems and methods utilize machine learning. For example, systems and methods may utilize AI models in machine learning to automate diagnosis, for example utilizing deep learning models. The systems and methods described herein may be implemented as standalone or integrated applications for processing X-ray tomography images using artificial intelligence models associated with image data.

Usually, one of methods includes obtaining a model that takes X-ray scans of a human lung or breast as input and outputs the diagnosis of this lung or breast. The diagnosis includes the prediction of the lung, breast disease or nodule, lesion condition, the prediction of the severity level and the detection of the important features in the input of X-ray scan image.

Figure 3:
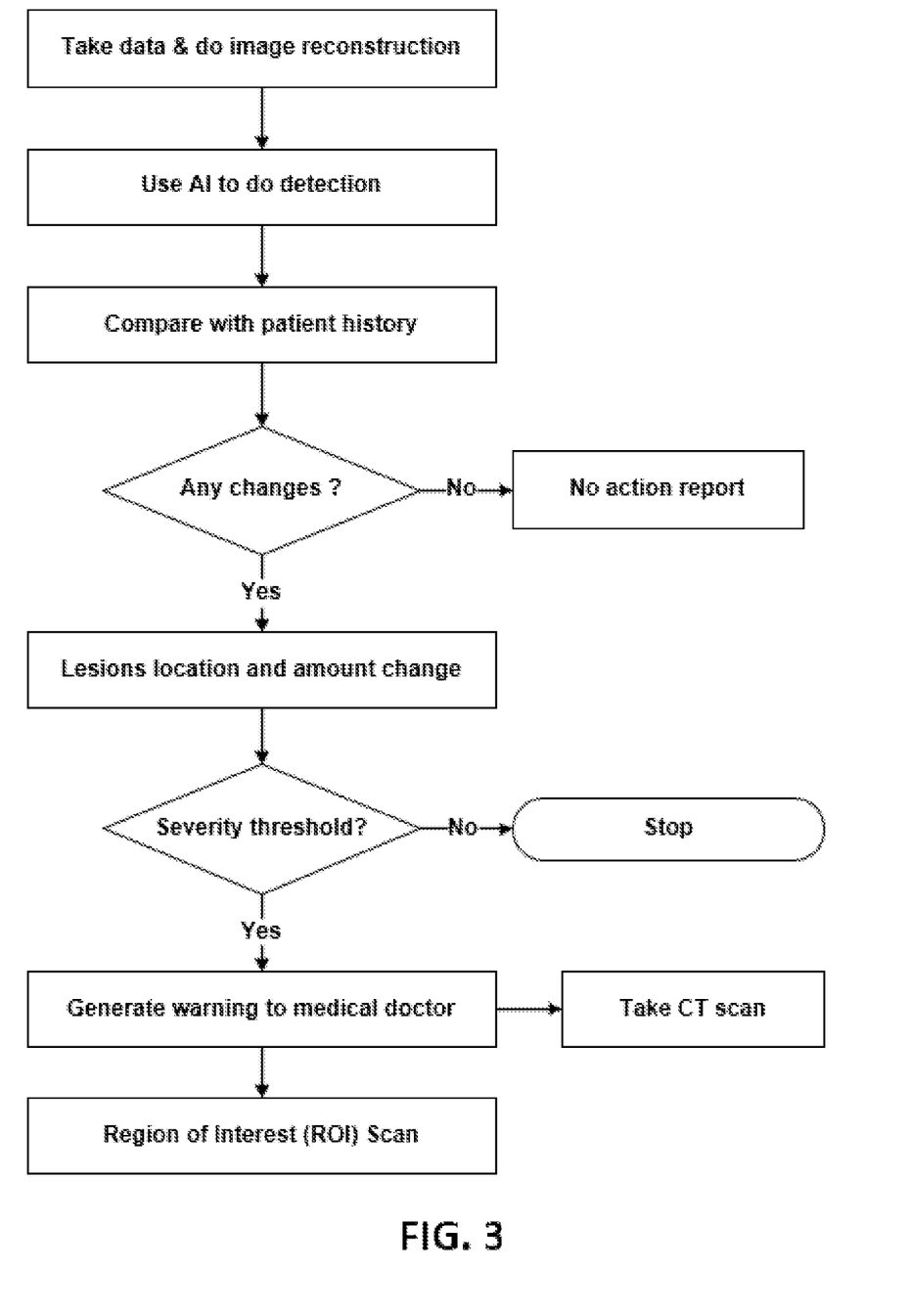
FIG. 3 shows a flow chart of an exemplary AI based diagnosis process performed with the multiple X-ray source-in-motion tomosynthesis imaging system.

FIG. 3 shows an exemplary flow chart of AI based diagnosis at the X-ray tomosynthesis imaging system after machine learning. In general, before a patient take comprehensive X-ray scan, previous record of patient or other standard information for ordinary healthy person is already available either at local computer or at a health network. The first step is that a patient is scanned to generate data. Imaging acquisition can be progressive. Then the second step is that system immediately does image construction based on the progressive scan. The third step is to use artificial intelligence (AI) to compare with available knowledge regarding the patient, such as patient medical history, etc. The fourth step is to let AI make the decision. If there are no changes, it may indicate that the patient scan is normal and then the process will stop. If there are changes in the scan indicative of one or more lesions, AI will decide to find out the extent of the new lesion detected and the location of each lesion. Then AI also makes the decision of how serious it is. If it is not serious, then the process exits. If it is serious, AI will generate a warning to doctors and send recommendations to do a more extensive scan including a region of interest (ROI) scan or CT scan.

A patient scan generates raw data. To process the data, it is necessary to compare the acquired data with normal data in reference memory unit. In order to make sure that raw data meets the medical diagnostic criteria, constructs statistical models for the location of each anomaly in 3D space based on the geometrical configuration of the device or device's component in relation to the patient. Based on the statistical models, it computes the decision whether to take a full scan or partial scan. Then when it decided to take full scan, multiple pulsed source-in-motion tomosynthesis imaging system proceeds to take an image, which includes exposing multiple pulsed sources, detector, and tube elements for imaging. This can be done either simultaneously or sequentially, but preferably simultaneously.

Reconstruction is preferably performed in accordance with multiple pulsed source-in-motion tomosynthesis imaging system techniques. As a result, a plurality of images of a first object or a first patient taken from a plurality of different angles are obtained as reconstructed tomosynthesis image set. The patient's first object is positioned relative to a substantially stationary radiation source and a detector as previously described. Subsequently, a radiation source control system, also referred to as a tracking system, generates a pulsed X-ray radiation pattern to direct X-ray radiation from a multiple pulsed sources toward the patient image. In the preferred embodiment, the pulsed X-ray radiation pattern corresponds to a collimated polygonal ring beam.

AI detection determines whether or not there is a change in the structure of the system. If the AI detection determines that there is no change in the system's structure, then the AI transmits, to the X-ray detector, an instruction to end the progressive scan and acquire a final image. The progressive scan and acquisition of the final image may be repeated as necessary to acquire one or more images. AI diagnosis module determines whether or not there is a lesion in the patient using various parameters including without limitation: Dose values; Partial Volume Effect (PVE); Digital Signal (DS); Contrast (C); (SNR); Image Noise; Thickness; Histogram Variance; Pause time; X-ray scatter; Attenuation factor; Resolution and many others. AI scan technique performs scan and analysis locally and informs other locations via network and will use their processing power and large storage for this analysis.

In comparison with patient history or current data, a threshold is set in a decision block. The AI scans a plurality of ROIs from an acquired image. In an area identification step, the AI locates a possible lesion from one or more of the ROIs and records its location for a process block. In a detection reliability decision step, the AI determines if the recorded location is within the threshold. If the recorded location is not within the threshold, the process ends. If the recorded location is within the threshold, the process continues to a severity classification decision step. In the severity classification decision step, the AI determines if the recorded location has a high or low severity rating. If the recorded location has a high severity rating, the process continues to a second area identification step. In the second area identification step, the AI may scan one or more additional ROIs from the acquired image to confirm the presence of the lesion. If the recorded location has a low severity rating, the process continues to a recommendations step. In the recommendations step, the AI recommends a scan of the lesion. The scan of the lesion may be performed by a standard scan of a full CT scan, a region of interest (ROI) scan, a focused scan of multiple channels, and so on.

AI will report back to human doctor and give recommendations about possible next course of action and, in general, keep a virtual (networked) health care professional in the loop and control at all times.

The system with the artificial intelligence (AI) for X-ray source-in-motion diagnosis procedure can operate with different types of scan in this system. For example, one system applies a progressive scan, and the other is a sequential scan. A progressive scan is where each data acquired in each snapshot is used to create the next image in a stack of images. The procedure will continue until sufficient data is collected to cover the region of interest (ROI). If the lesion is static, it will be much easier to diagnose using a progressive scan since no or little information about the history of the lesion is required. If the lesion is moving, the progressive scan can follow the lesion but will require high-frequency data acquisition, significantly increasing the dose. Progressive scan can also be performed in three phases. First, raw data is collected to construct the initial normal model. Second, the pre-processed data is collected to refine the normal model. Third, the post-processed data is collected to refine the normal model again if needed. While taking x-ray instrument image data, artificial intelligence analyzes patient responses, compares current condition with the patient history and other patient information that may become part of a patient. It reports lesions location changes, sets severity threshold and warning status, generates treatment information. It also recommends to a region of interest (ROI) scan, a complete CT scan, or other health care professionals and specialists.

This application uses a multiple pulsed source-in-motion tomosynthesis imaging system. This application is a method for a faster and more accurate X-ray diagnostics apparatus by applying AI for real-time decision-making and scanning processes. A conventional X-ray diagnostic apparatus works as follows: take raw data, the image acquired raw data to a model, build a model of normal operation mode, build a model of different failure modes, acquire the real-time data from the X-ray detector array, analyze the real-time data based on each model, detect if there is an anomaly. In contrast, the presented invention system does as follows: using an AI supercomputer to construct a model of the performance of each subsystem in a normal operating mode and each of a plurality of different possible failure modes. Then, the AI dynamically predicts the performance of each subsystem based upon the response of each of the models to dynamically changing operating conditions, compares the actual performance and result of each subsystem with the dynamically predicted performance thereof in each of the normal and possible failure modes, and determines the operating condition based on these comparisons. Furthermore, multiple pulsed source-in-motion tomosynthesis imaging systems can perform nearly real-time low dose X-ray scans. Multiple pulsed source-in-motion tomosynthesis imaging systems can also perform 4-dimensional scan or progressive scan.

The image data obtained from each partial-scan may be evaluated by Artificial Intelligence to detect possible lesions in various body parts, for example, lung nodule and breast cancer in this case. Based on the detection, the present disclosure will generate warning information for doctors to decide if they need to take an ROI scan or do a CT scan or some other comprehensive diagnostic tools.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. The various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open-ended as opposed to limiting. As examples of the foregoing: the term "including" should be read as meaning "including, without limitation" or the such as; the term "example" is used to provide exemplary instances of the item in discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of diagnosis using artificial intelligence with a multiple pulsed X-ray source-in-motion tomosynthesis imaging system, the method comprising:
   acquiring a progressive scan of a patient using a multiple pulsed source-in-motion tomosynthesis imaging system mounted on a structure in motion to form an array of X-ray sources that move simultaneously relative to an object on a pre-defined arc track at a constant speed as a group, each X-ray source moves around a position relative to the group at a predetermined distance, and when an X-ray source has a speed equal to group speed but with opposite moving direction, the X-ray source and an X-ray flat panel detector are activated through an external exposure control unit to stay standstill momentarily;
   performing image construction based on the progressive scan;
   using artificial intelligence (AI) to determine a severity of a lesion by comparing differences between a prior scan and the progressive scan; and
   determining with the AI a location of the lesion and lesion growth.

2. The method of claim 1, comprising using artificial intelligence (AI) to make decision to stop if there is no change and otherwise determining a severity of a lesion anomaly and if so recommending additional scans with a predetermined region of interest (ROI) scan or a CT scan.

3. The method of claim 1, comprising generating a warning and sending one or more recommendations to examine a region of interest (ROI) scan or CT scan.

4. The method of claim 1, comprising using AI to construct a model of the performance of the imaging system in a normal operating mode and each of a plurality of different possible failure modes.

5. The method of claim 4, comprising:
   dynamically predicting the performance of the X-ray source based upon the response of each of the models to dynamically changing operating conditions,
   comparing the actual performance and result of the X-ray source with the dynamically predicted performance thereof in each of the normal and possible failure modes, and
   determining the operating condition based on these comparisons.

6. The method of claim 1, comprising performing near real-time low dose X-ray scans.

7. The method of claim 1, comprising performing a 4-dimensional scan with a multiple pulsed source-in-motion tomosynthesis imaging system.

8. The method of claim 2, wherein during taking X-ray instrument image data, analyzing patient responses, comparing current condition with the patient history and patient information.

9. The method of claim 1, comprising reporting lesion location changes, setting a severity threshold and warning status, and generating treatment information.

10. The method of claim 1, comprising recommending a region of interest (ROI) scan or a complete CT scan, or one or more health care professionals and specialists based on the location of the lesion and lesion growth.

11. An X-ray tomosynthesis diagnosis system using artificial intelligence, comprising:
   a multiple pulsed X-ray source-in-motion tomosynthesis imaging system mounted on a structure in motion to form an array of X-ray sources that move simultaneously relative to an object on a pre-defined arc track at a constant speed as a group, each X-ray source moves around a position relative to the group at a predetermined distance, and when an X-ray source has a speed equal to group speed but with opposite moving direction, the X-ray source and an X-ray flat panel detector are activated through an external exposure control unit to stay standstill momentarily; and
   a processor coupled to the multiple pulsed X-ray source-in-motion tomosynthesis imaging system, the processor running code for:
      acquiring a progressive scan of a patient using the multiple pulsed X-ray source-in-motion tomosynthesis imaging system;
      performing image construction based on the progressive scan;
         using artificial intelligence (AI) to determine a severity of a lesion by comparing a prior scan with the progressive scan; and
      determining a location of the lesion and lesion growth with the AI.

12. The system of claim 11, comprising artificial intelligence (AI) to make decision to stop if there is no change and otherwise determining the severity of a lesion anomaly and if so recommending additional scans with a predetermined region of X-ray interest (ROI) scan or a CT scan.

13. The system of claim 11, comprising code for generating a warning and sending one or more recommendations to examine a region of X-ray interest (ROI) scan or CT scan.

14. The system of claim 11, comprising code for using AI to construct a model of the performance of each multiple pulsed X-ray source-in-motion tomosynthesis X-ray source in a normal operating mode and each of a plurality of different possible failure modes.

15. The system of claim 11, comprising code for:
dynamically predicting the performance of the X-ray source based upon the response of one or more models to dynamically changing operating conditions,
comparing the actual performance and result of the X-ray source with the dynamically predicted performance thereof in each of the normal and possible failure modes, and
determining the operating condition based on these comparisons.

16. The system of claim 11, comprising code for performing nearly real-time low dose X-ray imaging scans.

17. The system of claim 11, comprising code for performing a 4-dimensional scan with a multiple pulsed source-in-motion tomosynthesis imaging system.

18. The system of claim 11, wherein during taking X-ray instrument image data, comprising code for analyzing patient responses, comparing current condition with the patient history and patient information.

19. The system of claim 11, comprising code for reporting lesion location changes, setting a severity threshold and warning status, and generating treatment information.

20. The system of claim 11, comprising code for recommending a region of interest (ROI) scan or a complete CT scan, or one or more health care professionals and specialists based on the location of the lesion and lesion growth.

\* \* \* \* \*